United States Patent
Kobayashi et al.

[11] Patent Number: 5,999,591
[45] Date of Patent: *Dec. 7, 1999

[54] MEASURING INSTRUMENT AND MEASURING METHOD

[75] Inventors: Shigeki Kobayashi, Yotsukaido; Kazuhito Ishihara, Tokyo, both of Japan

[73] Assignee: Terumo Kabushiki Kaisha, Tokyo, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/960,348

[22] Filed: Oct. 29, 1997

[30] Foreign Application Priority Data

Oct. 29, 1996 [JP] Japan .................................. 8-287154

[51] Int. Cl.$^6$ ........................................... H05G 1/28
[52] U.S. Cl. ............................................ 378/163; 378/162
[58] Field of Search .................................. 378/162, 163, 378/164

[56] References Cited

U.S. PATENT DOCUMENTS

| | | | |
|---|---|---|---|
| 3,991,310 | 11/1976 | Morrison . | |
| 4,341,220 | 7/1982 | Perry | 606/130 |
| 4,618,978 | 10/1986 | Cosman | 378/164 |
| 5,216,700 | 6/1993 | Cherian | 378/163 |
| 5,260,985 | 11/1993 | Mosby | 378/164 |
| 5,822,396 | 10/1998 | Navab et al. | 378/207 |

FOREIGN PATENT DOCUMENTS

| | | |
|---|---|---|
| 4-102465 | 4/1992 | Japan . |
| 5-68677 | 3/1993 | Japan . |
| 5-68678 | 3/1993 | Japan . |
| 7-313611 | 12/1995 | Japan . |
| WO 93/08737 | 5/1993 | WIPO . |

*Primary Examiner*—David Vernon Bruce
*Attorney, Agent, or Firm*—Burns, Doane, Swecker & Mathis, LLP

[57] ABSTRACT

To provide a method and an instrument capable of easily and accurately measuring a size of an affected part present in a body of a patient, there is provided a measuring instrument 1 including at least four sheets of acrylic plates having indices of a substance of X-ray image forming performance of metal balls 2 and 3, metal wires and the like in which sets of two sheets of the acrylic plates are arranged in parallel to each other and a space defined by the sets of acrylic plates arranged in parallel, is provided with an interval capable of receiving a part of a patient to be measured, such as the head or the like.

6 Claims, 5 Drawing Sheets

MEASURING INSTRUMENT AND MEASURING METHOD

BACKGROUND OF THE INVENTION

1. Field of the Invention

The present invention relates to a measuring instrument and a method of measuring by using the measuring instrument for measuring a size of an affected part of an organ in a body, vessel, vas and celom such as aneurysm, artery and vein malformation, tumor or the like by using an X-ray photographing device, and particularly relates to a measuring instrument and a measuring method using the measuring instrument for measuring an actual size of an affected part in a brain.

2. Description of the Related Art

It is important in the field of brain surgery to measure a size, such as a diameter, of a brain artery aneurysm, a diameter of a vessel, a size of a brain artery and vein malformation (AVM) or the like in considering selection of an optimum coil size in a brain artery aneurysm plugging operation, an amount of a plugging drug to be used, adaptation of a γ knife with respect to AVM and the like. Conventionally, in the heart vessel imaging field, a catheter, a guide wire or the like is inserted into a vicinity of an affected part and X-ray imaging is performed to calculate a diameter of a vessel from a proportion of the size of the instrument to the diameter of the vessel. However, when a danger of laceration is conceivable as, for example, in brain aneurysm, a catheter having a large diameter cannot be advanced to an affected part.

In such a case, there has been used a method in which a metal ball or the like is placed outside of a body as an index and a size of an affected part is approximately calculated from a proportion of the diameter of the metal ball to the size of the affected part.

However, when the index placed outside of a body and the affected part present inside of the body are made to be simply proportional to each other, since X-rays diverged radially, the magnifications of the index and the affected part in the X-ray vessel photographing, are changed in accordance with a distance between an X-ray tube (light source) and an imaging intensifier (I.I.) (light receiving portion) and positions of the index and the affected part and therefore, there causes an error between a calculation result and an actual size depending on the position (depth) of the affected part. Thus, this method is devoid of accuracy.

SUMMARY OF THE INVENTION

An object of the present invention is to avoid the problems of the prior art methods and apparatus, while providing accurate measurements of the affected body part.

In order to achieve the above-described objects, it is preferable that a measuring instrument of the present invention have the following constitution:

(1) A measuring instrument including at least four sheets of X-ray permeable substrates each provided with indices formed by a substance having an X-ray image forming characteristic, and wherein sets of two sheets of the substrates are arranged in parallel to each other and a space between the sets of the parallelly arranged substrates is provided with an interval capable of receiving an object to be measured.

(2) The measuring instrument according to (1), wherein the substrates form a polygonal shape and inside of the polygonal shape is provided with a space capable of receiving an object to be measured.

Further, acrylic plates are preferable used as the substrates capable being permeated by X-ray and it is preferable to constitute the substrates in a frame-like square shape having a side length of substantially 25 cm such that the four sheets of acrylic plate can surround the head of an examined person.

Further, it is preferable with respect to the indices in (1) that graduations (a scale) made of iron at predetermined intervals are provided at one of a set of parallel sides of the measuring instrument and metal balls each having a predetermined diameter are provided at predetermined intervals at the other one of the set.

Further, it is preferable that a measuring method of the present invention is provided with the following constitution:

(3) A method of measuring an actual size of a measured object in an X-ray image, said method comprising:
a first step of irradiating X-rays to a measured part from a first direction, arranging a first measuring instrument having indices formed by a substance of an X-ray image forming characteristic such that the first measuring instrument is orthogonal to the X-rays irradiated from the first direction and photographing the measured part;
a second step of irradiating X-rays to a measured part from a second direction different from the first direction, arranging a second measuring instrument having indices formed by a substance of an X-ray image forming characteristic such that the second measuring instrument is orthogonal to the X-rays irradiated from the second direction and photographing the measured part; and
a third step of calculating the size of the measured object by a proportional expression using a value formed by measuring a size of the measured object in a first image obtained by the first step by intervals of the indices in the image and a value showing a positional relationship between the first measuring instrument and the measured part obtained from the first image and a second image provided by the second step.

(4) The method according to (3), wherein the first measuring instrument and the second measuring instrument are integrally formed.

(5) The method according to (3), wherein the proportional expression is as shown below:

$$\beta = \alpha + (b-a)\alpha x / La$$

where notation $\beta$ designates a size of the measured object in a horizontal direction and notation "$\alpha$" designates a size of the measured object in the horizontal direction measured by the indices on the first image, notation "a" designates one unit of the indices in the first measuring instrument, notation "b" designates a value formed by enlarging the one unit of the indices, notation "x" designates a distance between the first index and the measured object, and notation L designates a distance between the first measuring instrument and an X-ray photographing portion.

(6) The method according to (4), wherein the first measuring instrument and the second measuring instrument constitute an integrated measuring instrument by parallelly arranging in sets of two sheets at least the four sheets of X-ray permeable substrates each provided with the indices formed by the substance of the X-ray image forming performance; and wherein the proportional expression is as shown below:

$$\beta = \alpha + (b-a)\alpha x/La$$

where notation β designates a size of the measured object in a horizontal direction, notation "α" designates a size of the measured object in the horizontal direction measured by the indices on the first image, notation "a" designates one unit of the indices in the first measuring instrument, notation "b" designates a value formed by measuring a value formed by enlarging the one unit of the indices on the first image, by images of the indices of an instrument arranged in parallel to the first measuring instrument, notation "x" designates a distance between the first index and the measured object and notation L designates a distance between the first measuring instrument and the instrument arranged in parallel to the first measuring instrument.

DETAILED DESCRIPTION

The present invention will be described by way of a specific embodiment of the present invention with reference to the attached drawings as follows. Incidentally, the following embodiment will be described for explaining the present invention and the present invention is not restricted to only this embodiment.

Figure 1:
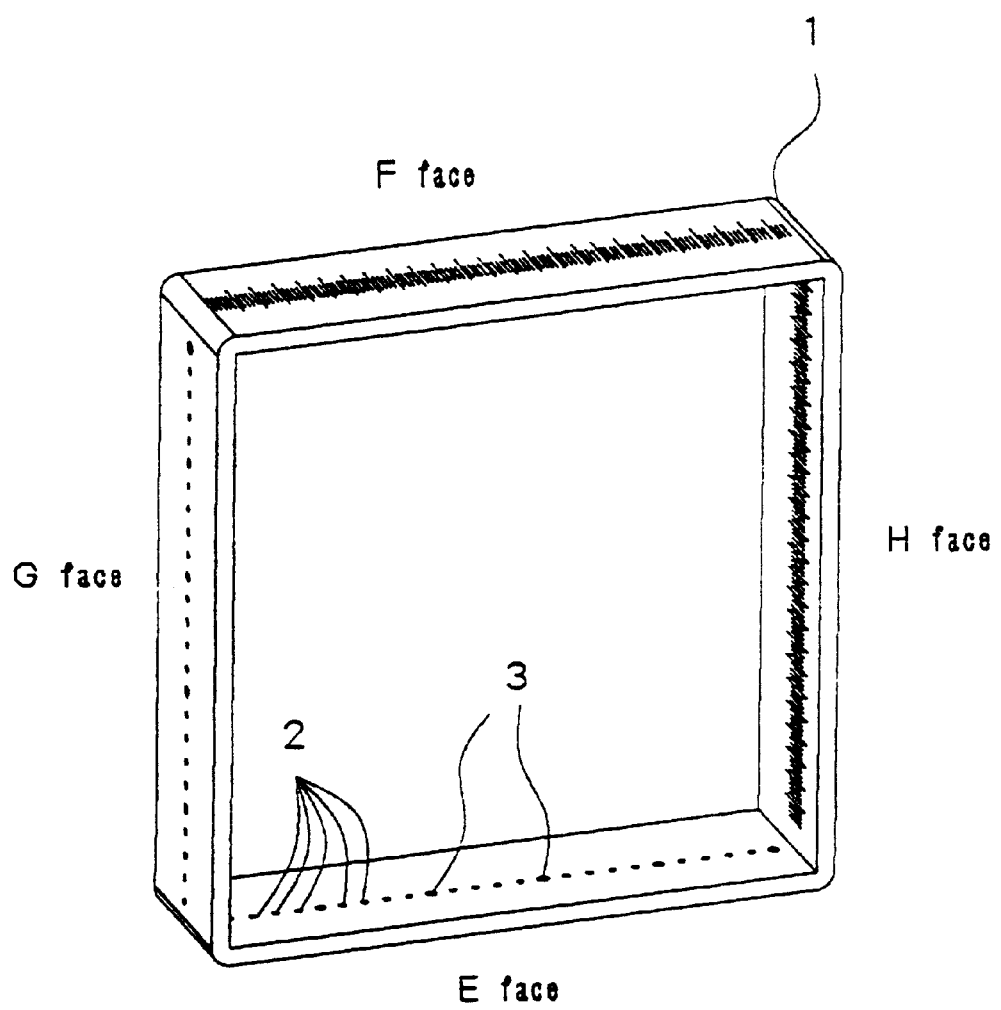
FIG. 1 is a perspective view of a measuring instrument according to the present invention.

FIG. 1 is a perspective view of a measuring instrument according to the embodiment. In FIG. 1, a measuring instrument 1 is formed with four sheets of acrylic plates respectively constituting E face, F face, G face and H face in a square shape. The four sheets of the acrylic plates each is provided with a thickness of 3 mm, a width of 40 mm and a side length of 250 mm, for example. Among them, metal balls 2 (made of iron) having the diameter of 2 mm are arranged at intervals of 1 cm and metal balls 3 having the diameter of 3 mm are arranged at intervals of 5 cm as indices in E face and G face. Further, metal wires (made of iron) having the diameter of 0.5 mm are arranged at intervals of 2 mm in F face and H face. Most of the metal wires are provided with the length of 20 mm and the metal wires each have the length of 30 mm are arranged at every fifth line, for example. The different indices are provided for each parallel set such that the indices of either one of the faces can easily be confirmed in observing an X-ray image. Further, although not illustrated, numerals indicating respectively distances from end portions of the respective faces are printed to the indices by an X-ray unpermeable metal.

Figure 2:
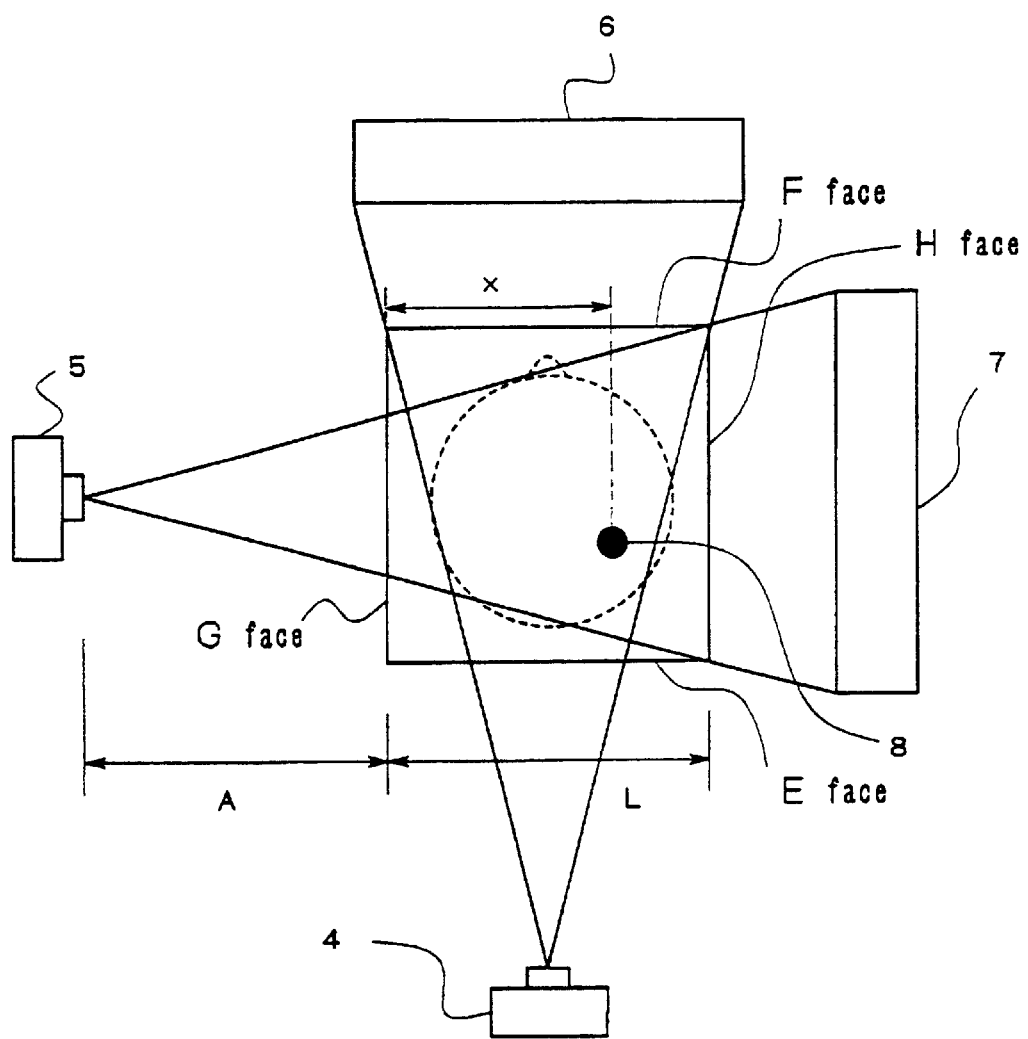
FIG. 2 is a view for explaining a state where the measuring instrument of the present invention is mounted to an examined person and instruments for X-ray photographing are arranged.

Next, a specific explanation will be given of a method of calculating a size of an affected part. FIG. 2 is a view for explaining a state where the measuring instrument 1 shown by FIG. 1 is mounted to the head of a patient and X-rays are irradiated. As shown by FIG. 2, X-rays are irradiated from two directions on the sides of E face and G face by X-ray tubes 4 and 5 by which respective X-ray images are provided by X-ray receiving portions 6 and 7 which are imaging intensifiers (I.I.) installed at the sides of F face and H face. As a device for irradiating X-rays in two directions in such a manner, a device known as C arm device or pipe lane device can be used. In the drawing, numeral 8 designates an affected part (aneurysm) imaged by injecting an image forming agent into the affected vein. Further, notation A designates a distance from the X-ray tube 5 to G face of the measuring instrument 1 and notation L designates a distance between G face and H face of the measuring instrument 1. Further, notation x designates a distance between the affected part 8 and G face.

Figure 3:
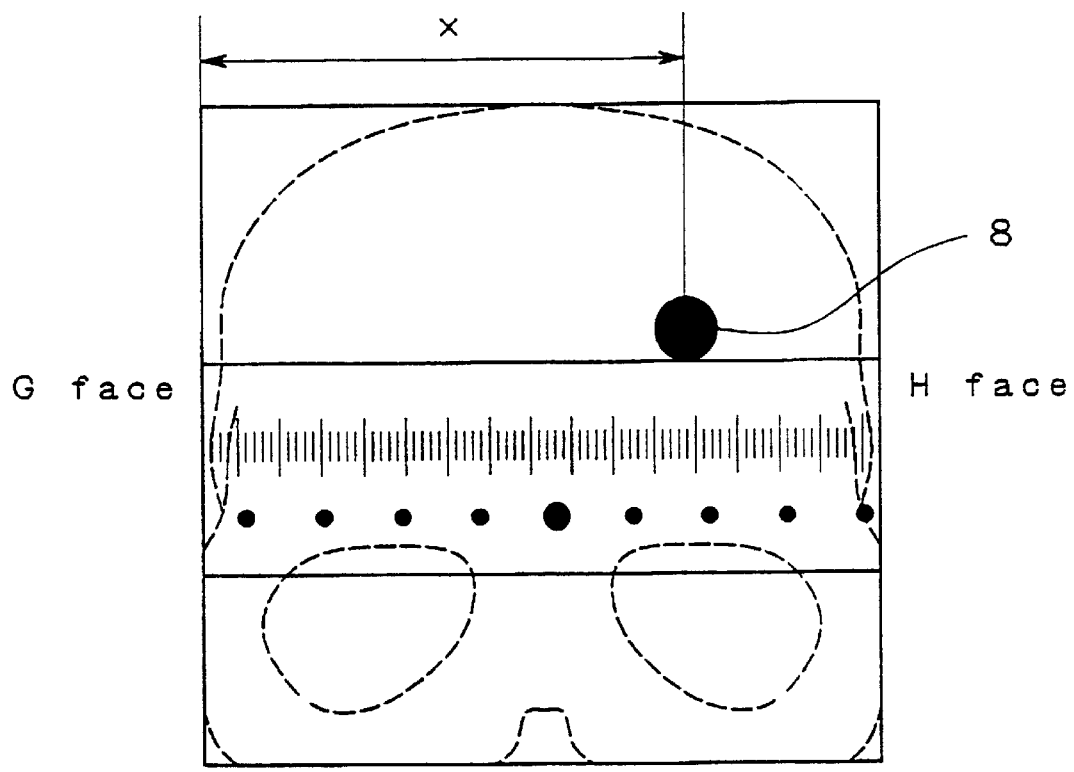
FIG. 3 is a view showing an image photographed by an X-ray receiving portion 6.
Figure 4:
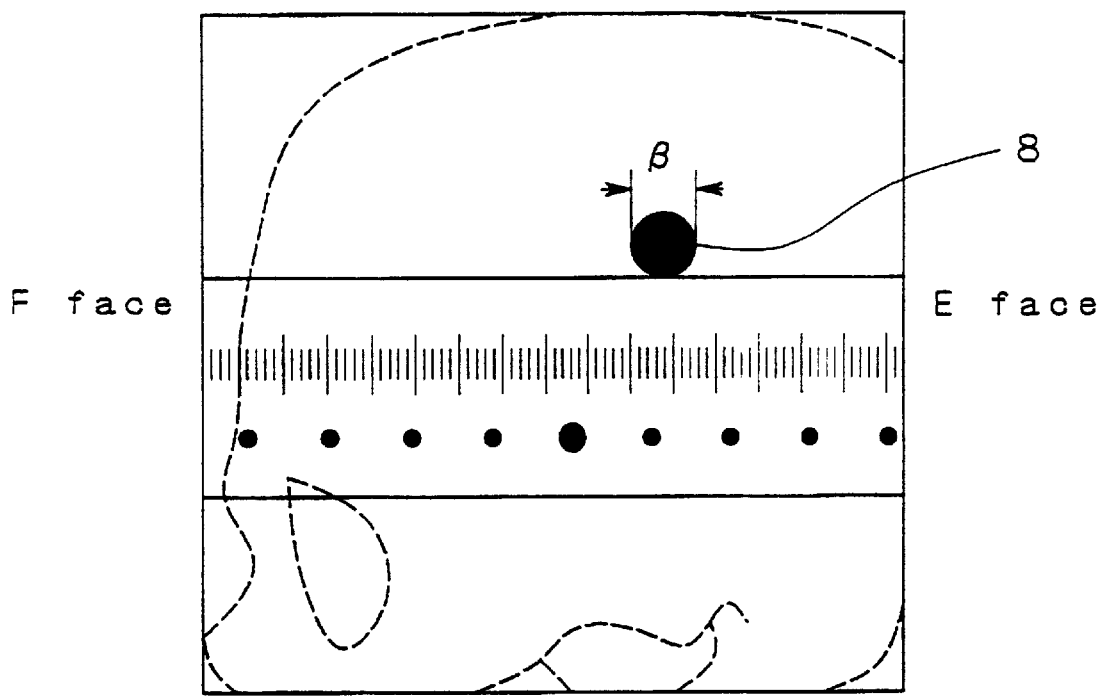
FIG. 4 is a view showing an image photographed by an X-ray receiving portion 7.

FIG. 3 and FIG. 4 show images provided by the X-ray receiving portions 6 and 7 in this way. FIG. 3 shows an image formed by detecting an X-ray irradiated by the X-ray tube 4 from the direction of E face by the X-ray receiving portion 6 on the side of F face. FIG. 4 shows the image formed by detecting an X-ray irradiated by the X-ray tube 5 from the direction of G face by the X-ray receiving portion 7 on the side of H face. In these images, the indices respectively provided on the two parallel faces of the measuring instrument 1 and the formed image of the affected part 8 can be confirmed. Images of the metal balls constituting the indices on the side of the X-ray tube and images of the metal wires constituting the indices on the side of the receiving portion, are photographed with different magnifications with respect of the intervals and the diameters since the irradiated X-ray diverges radially.

Here, when the actual diameter of the metal ball is designated by notation "a" and the diameter of the image of the same metal ball which can be confirmed by graduations of the metal wires in the image of FIG. 4, is designated by notation "b", the following equation is established.

$$a:b = A:(A+L) \tag{1}$$

Further, when a value of the diameter in the horizontal direction of the image of the affected part 8 provided by FIG. 4 which is measured by the graduations of the metal balls in the image, is designated by notation α and a size (diameter in the horizontal direction) of the actual affected part 8 to be calculated is designated by notation β, similar to Equation (1), the following equation is established. Incidentally, notation x represents a distance from G face to the affected part 8 as shown by FIG. 3.

$$\alpha:\beta = A:(A+x) \tag{2}$$

Summarizing Equation (1) and Equation (2), the following equation is obtained.

$$\beta = \alpha + (b-a)\alpha x/La \tag{3}$$

Since a, b, α, and L are values which have already been obtained, they can be put into Equation (3).

Figure 5:
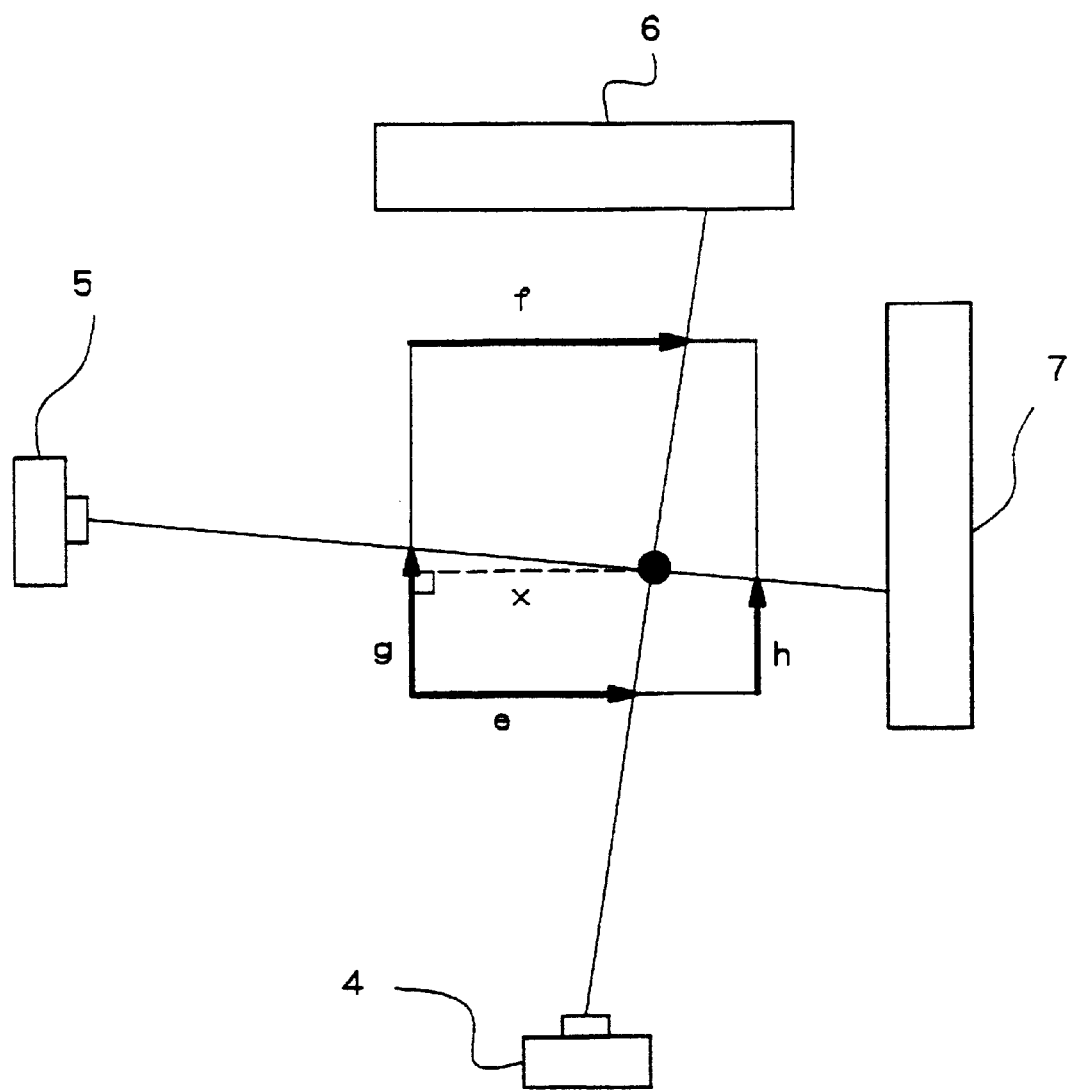
FIG. 5 is a view for explaining coordinate axes for calculating a distance x.

Next, an explanation will be given of the way to calculate the distance x from G face to the affected part 8. FIG. 5 is formed by simplifying FIG. 2 for explaining the coordinate axes for calculating the distance x. In FIG. 5, when a straight line connecting the X-ray tube 5 and the affected part 8 is represented by an equation with E face as x axis and G face as y axis, the equation is as follows.

$$Y = (h-g)X/L + g \tag{4}$$

Here, notation "h" designates a distance between E face and the affected part 8 measured by the graduations of the metal wires in the image of FIG. 4 and notation "g" designates a distance between E face and the affected part 8 measured by the graduations of the metal balls. These distances can be read by numerals (not illustrated) provided along with the above-described indices.

Similarly, when a straight line connecting the X-ray tube 6 and the affected part 8 is represented by an equation, the equation is as follows.

$$Y=L(X-e)/(f-e) \quad (5)$$

where notation "e" designates a distance from G face to the affected part 8 measured by the graduations of the metal wires and notation "f" designates a distance from G face to the affected part 8 measured by the graduations of the metal balls. Also, these distances can be read similarly by numerals (not illustrated) provided along with the above-described indices.

An intersection of the two straight lines designated by Equation (4) and Equation (5) indicates the coordinates of the affected part 8 and therefore, the distance x to be calculated is shown by the following equation.

$$x=L(Le+(f-e)g)/(L^2-(h-g)(f-e)) \quad (6)$$

In this way, the size β of the affected part 8 can be calculated by putting respective values into Equation (3). Further, when Equation (3) and Equation (6) are previously formulated in a computer or the like, the size β can easily be obtained only by inputting the respective numerical values.

Further, the indices made of metal according to the embodiment are not needed to stick to combinations of metal wires and metal balls but any indices may be used so far as they can be differentiated by observing an obtained image. As other example, it is conceivable to shift positions of indices on acrylic plates. Instead of providing the indices on the acrylic plates on the sides of light receiving portions, respective numerical values of an obtained image (photograph, film or an image displayed on a monitor) may be measured directly by a scale. In that case, distances between light receiving portions and measuring instruments are previously measured and a numerical value in place of the length L of the measuring instrument 1 may be used based thereon.

Further, although a method of fixing the measuring instrument according to the present invention at the head of an examined person is arbitrary, a fixing part of a belt, a cap or the like may be installed to the measuring instrument by using an X-ray permeable material. Also, although according to the embodiment, the instrument has been described as an instrument for the head, by enlarging the instrument, an instrument similarly measuring other portions of a patient can be obtained.

As has been explained, according to the present invention, the measuring instrument provided with the indices surrounding a measured part can be obtained and accordingly, by calculating a ratio of the magnifications of the X-ray images from two directions of the measured part, the size of the affected part can simply and accurately be measured only by measuring the distances on the images. Further, according to the present invention, the magnifications can be corrected even when the affected part is displayed at any position on the images without being particular about the geometrical arrangement of the photographing device and, therefore, no restriction is imposed in photographing operation in measurement photographing. Therefore, the invented device is very practical since the size of an affected part can be measured simply even with a complicated vessel image forming inspection and Interventional Radiography (IVR).

The present invention has been described by way of exemplary embodiments. Variations and modifications will occur to those skilled in the art without departing from the spirit and scope of the present invention. For instance, rather than iron s the material for the indices, any suitable X-ray impermeable or attenuating material can be used. Also, rather than wire sections or balls, the indices can be printed or imposed in X-ray impermeable material on the sheets. Also, materials other than acrylic can be used, provided the material is largely X-ray permeable relative to the object being studied and the indices placed thereon. Naturally, other dimensions than those listed above could be used.

What is claimed is:

1. A measuring instrument comprising:

at least four sheets of X-ray permeable substrates each provided with indices formed by a substance having an X-ray image forming characteristic; and wherein sets of two sheets of the substrates are arranged in parallel to each other and a space between the sets of the parallelly arranged substrates is provided with an interval capable of receiving an object to be measured.

2. The measuring instrument according to claim 1, wherein the substrates form a polygonal shape and inside of the polygonal shape is provided with a space capable of receiving an object to be measured.

3. A method of measuring an actual size of a measured object in an X-ray image, said method comprising:

a first step of irradiating X-rays to a measured part from a first direction, arranging a first measuring instrument having indices formed by a substance of an X-ray image forming characteristic such that the first measuring instrument is orthogonal to the X-rays irradiated from the first direction and photographing the measured part;

a second step of irradiating X-rays to a measured part from a second direction different from the first direction, arranging a second measuring instrument having indices formed by a substance of an X-ray image forming characteristic such that the second measuring instrument is orthogonal to the X-rays irradiated from the second direction and photographing the measured part; and a third step of calculating the size of the measured object by a proportional expression using a value formed by measuring a size of the measured object in a first image obtained by the first step by intervals of the indices in the image and a value showing a positional relationship between the first measuring instrument and the measured part obtained from the first image and a second image provided by the second step.

4. The method according to claim 3, wherein the first measuring instrument and the second measuring instrument are integrally formed.

5. The method according to claim 3, wherein the proportional expression is as shown below:

$$\beta=\alpha+(b-a)\alpha x/La$$

where notation β designates a size of the measured object in a horizontal direction and notation α designates a size of the measured object in the horizontal direction measured by the indices on the first image, notation "a" designates one unit of the indices in the first measuring instrument, notation "b" designates a value formed by enlarging the one unit of the indices, notation "x" designates a distance between the first index and the measured object, and notation L designates a distance between the first measuring instrument and an X-ray photographing portion.

6. The method according to claim 4:

wherein the first measuring instrument and the second measuring instrument constitute an integrated measuring instrument by parallelly arranging in sets of two sheets at least the four sheets of X-ray permeable substrates each provided with the indices formed by the substance of the X-ray image forming performance; and wherein the proportional expression is as shown below:

$$\beta = \alpha + (b-a)\alpha x / La$$

where notation $\beta$ designates a size of the measured object in a horizontal direction, notation $\alpha$ designates a size of the measured object in the horizontal direction measured by the indices on the first image, notation "a" designates one unit of the indices in the first measuring instrument, notation "b" designates a value formed by measuring a value formed by enlarging the one unit of the indices on the first image, by images of the indices of an instrument arranged in parallel to the first measuring instrument, notation "x" designates a distance between the first index and the measured object and notation L designates a distance between the first measuring instrument and the instrument arranged in parallel to the first measuring instrument.

* * * * *